US007271313B2

(12) United States Patent
Shen (10) Patent No.: US 7,271,313 B2
(45) Date of Patent: Sep. 18, 2007

(54) PRESENILIN-DEFICIENT MOUSE MODEL OF AGE-DEPENDENT NEURODEGENERATION AND COGNITIVE LOSS

(75) Inventor: Jie Shen, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 636 days.

(21) Appl. No.: 10/409,672

(22) Filed: Apr. 9, 2003

(65) Prior Publication Data

US 2004/0205836 A1 Oct. 14, 2004

(51) Int. Cl.
*A01K 67/027* (2006.01)
*C12N 15/00* (2006.01)

(52) U.S. Cl. .......................................... 800/18; 800/22
(58) Field of Classification Search .................... 800/18
See application file for complete search history.

(56) References Cited

U.S. PATENT DOCUMENTS 4,959,317 A  9/1990 Sauer ....................... 435/172.3

OTHER PUBLICATIONS

Doetschman, T. (1999) Interpretation of phenotype in genetically engineered mice. Laboratory Animal Science 49(2): 137-143.*
Donehower et al. (1995) Effects of genetic background on tumorigenesis in p53-deficient mice. Molecular Carcinogenesis 14: 16-22.*
Jacks et al. (1992) Effects of an Rb mutation in the mouse. Nature 359: 295-300.*
Jaenisch et al. (1988) Transgenic Animals. Science 240: 1468-1474.*
Kuehn et al. (1987) A potential animal model for Lesch-Nyhan syndrome through introduction of HPRT mutations into mice. Nature 326: 295-298.*
Moens et al. (1993) Defects in heart and lung development in compound heterozygotes for two different targeted mutations at the N-myc locus. Development 119: 485-499.*
Petridou et al. (2003) Heterogeneous inducible mammary-specific expression of JAB/SOCS1 in lactating transgenic mice is associated with no obvious phenotype, even at the cellular level. Transgenic Research 12: 693-706.*
Sigmund, CD (2000) Viewpoint: Are studies in genetically altered mice out of control? Arterioscler. Thromb. Vasc. Biol. 20: 1425-1429.*
Reece, RJ (2004) in Analysis of Genes and Genomes. John Wiley & Sons: Hoboken, New Jersey, p. 388, 389-440.*
Bear, "Homosynaptic Long-Term Depression: A Mechanism for Memory?," *Proc. Natl. Acad. Sci. USA* 96:9457-9458 (1999).
Borchelt, et al., "Familial Alzheimer's Disease-Linked Presenilin 1 Variants Elevate Aβ1-42/1-40 Ratio In Vitro and In Vivo," *Neuron* 17:1005-1013 (1996).
Brun, et al., "Regional Pattern of Degeneration in Alzheimer's Disease: Neuronal Loss and Histopathological Grading," *Histopathology* 5: 549-564 (1981).

Crook, et al., "A Variant of Alzheimer's Disease with Spastic Paraparesis and Unusual Plaques Due to Deletion of Exon 9 of Presenelin 1," *Nature Medicine* 4:452-455 (1998).
De Jonghe, et al., "Aberrant Splicing in the Presenilin-1 Intron 4 Mutation Causes Presenile Alzheimer's Disease by Increased Aβ42 Secretion," *Hum. Mol. Gen.* 8:1529-1540 (1999).
Donoviel, et al., "Mice Lacking Both Presenilin Genes Exhibit Early Embryonic Patterning Defects," *Genes & Dev.* 13:2801-2810 (1999).
Duff, et al., "Increased Amyloid-β42(43) in Brains of Mice Expressing Mutant Presenilin 1," *Nature* 383:710-713 (1996).
Elbashir, et al., "RNA Interference is Mediated by 21- and 22-Nucleotide RNAs," *Genes & Dev.* 15:188-200 (2001).
Elbashir, et al., "Duplexes of 21-Nucleotide RNAs Mediate RNA Interference in Cultured Mammalian Cells," *Nature* 411:494-498 (2001).
Gómez-Isla, et al., "Neuronal Loss Correlates with but Exceeds Neurofibrillary Tangles in Alzheimer's Disease," *Ann. Neurol.* 41:17-24 (1997).
Hanks, et al., "Region-Specific Stability of Dendritic Extent in Normal Human Aging and Regression in Alzheimer's Disease. I. CA1 of Hippocampus," *Brain Res.* 540:63-82 (1991).
Herreman, et al., "Total Inactivation of γ-Secretase Activity in Presenilin-Deficient Embryonic Stem Cells," *Nature Cell Biology* 2:461-462 (2000).
Herreman, et al., "Presenilin 2 Deficiency Causes A Mild Pulmonary Phenotype and No Changes in Amyloid Precursor Protein Processing but Enhances the Embryonic Lethal Phenotype of Presenilin 1 Deficiency," *Proc. Natl. Acad. Sci. USA* 96:11872-11877 (1999).

(Continued)

*Primary Examiner*—Anne-Marie Falk
(74) *Attorney, Agent, or Firm*—Michael A. Sanzo; Law Office of Michael A. Sanzo, LLC (57) ABSTRACT

The present invention is directed to recombinantly engineered mice that are deficient in the expression of both presenilin-1 and presenilin-2. The mice exhibit characteristics of age-dependent cognitive impairments and neurodegeneration similar to those seen in Alzheimer's disease patients. This presenilin-deficient mouse model can be used to screen compounds capable of slowing, preventing or reversing the progression of cognitive impairments and neurodegeneration. The invention is also directed to the development of treatments for Alzheimer's disease based on augmentation or restoration of presenilin function in the brain. On the basis of the findings described herein, the invention is further directed to the development of assays to detect functional presenilin deficiency in human individuals, preferably through analysis of presenilin substrates, which may provide biomarkers useful in the diagnosis of Alzheimer's disease.

9 Claims, 1 Drawing Sheet

OTHER PUBLICATIONS

Hiltunen, et al., "Identification of a Novel 4.6-kb Genomic Deletion in Presenilin-1 Gene Which Results in Exclusion of Exon 9 in a Finnish Early Onset Alzheimer's Disease Family: an *Alu* Core Sequence-Stimulated Recombination?," *Eur. J. Hum. Gen.* 8:259-266 (2000).

Hyman, et al., "Amyloid, Dementia and Alzheimer's Disease," *Curr. Opin. Neurol. Neurosurg.* 5:88-93 (1992).

Jo, et al., "Epigenetic Regulation of Gene Structure and Function with a Cell-Permeable Cre Recombinase," *Nat. Biotechnol.* 19:929-933 (2001).

Levy-Lehad, et al., "A Familial Alzheimer's Disease Locus on Chromosome 1," *Science* 269:970-973 (1995).

Li, et al., "Photoactivated γ-Secretase Inhibitors Directed to the Active Site Covalently Label Presenilin 1," *Nature* 405:689-694 (2000).

Rogaev, et al., "Familial Alzheimer's Disease in Kindreds with Missense Mutations in a Gene on Chromosome 1 Related to the Alzheimer's Disease Type 3 Gene," *Nature* 376:775-778 (1995).

Scheuner, et al., Secreted Amyloid β-Protein Similar to that in the Senile Plaques of Alzheimer's Disease Is Increased in vivo by the Presenilin 1 and 2 and APP mutations Lined to Familial Alzheimer's Disease, *Nature Med.* 2:864-870 (1996).

Shen, et al., "Skeletal and CNS Defects in Presenilin-1-Deficient Mice," *Cell* 89:629-639 (1997).

Sherrington, et al., "Cloning of a Gene Bearing Missense Mutations in Early-Onset Familial Alzheimer's Disease," *Nature* 375:754-760 (1995).

Steiner, et al., "A Loss of Function Mutatioin of Presenilin-2 Interferes with Amyloid β-Peptide Production and Notch Signaling," *J. Biol. Chem.* 274:28669-28673 (1999).

Terry, et al., "Physical Basis of Cognitive Alterations in Alzheimer's Disease: Synapse Loss Is the Major Correlate of Cognitive Impairment," *Ann. Neurol.* 30:572-580 (1991).

Tysoe, et al., "A Presenilin-1 Truncating Muation Is Present in Two Cases with Autopsy-Confirmed Early-Onset Alzheimer Disease," *Am. J. Hum. Genet.* 62:70-76 (1998).

Wilson, et al., "Presenilins Are Not Required for Aβ42 Production in the Early Secretory Pathway," *Nat. Neurosci.* 5:849-855 (2002).

Wolfe, et al., "Two Transmembrane Aspartates in Presenilin-1 Required for Presenilin Endoproteolysis and γ-Secretase Activity," *Nature* 398:513-517 (1999).

Yoo, et al., "Presenilin-Mediated Modulation of Capacitative Calcium Entry," *Neuron* 27:561-572 (2000).

Yu, et al., "APP Processing and Synaptic Plasticity in Presenilin-1 Conditional Knockout Mice," *Neuron* 31:713-726 (2001).

Yu, et al., "Heterogeneous Populations of ES Cells in the Generation of a Floxed Presenilin-1 Allele," *Genesis* 26:5-8 (2000).

Zhang, et al., "Presenilins are Required for γ-Secretase Cleavage of β-APP and Transmembrane Cleavage of Notch-1," *Nature Cell Biol.* 2:463-465 (2000).

* cited by examiner

Figure 1

SEQUENCE LISTING

<160> NUMBER OF SEQ ID NOS: 5

<210> SEQ ID NO 1
<211> LENGTH: 46
<212> TYPE: DNA
<213> ORGANISM: Mus musculus

<400> SEQUENCE: 1
actagtataa cttcgtataa tgtatgctat acgaagttat gctagc         46

<210> SEQ ID NO 2
<211> LENGTH: 21
<212> TYPE: DNA
<213> ORGANISM: Mus musculus

<400> SEQUENCE: 2
ggtttccctc catcttggtt g         21

<210> SEQ ID NO 3
<211> LENGTH: 20
<212> TYPE: DNA
<213> ORGANISM: Mus musculus

<400> SEQUENCE: 3
tcaactcctc cagagtcagg         20

<210> SEQ ID NO 4
<211> LENGTH: 46
<212> TYPE: DNA
<213> ORGANISM: Mus musculus

<400> SEQUENCE: 4
gctagcataa cttcgtatag catacattat acgaagttat actagt         46

<210> SEQ ID NO 5
<211> LENGTH: 21
<212> TYPE: DNA
<213> ORGANISM: Mus musculus

<400> SEQUENCE: 5
tctggaagta ggacaaaggt g         21

PRESENILIN-DEFICIENT MOUSE MODEL OF AGE-DEPENDENT NEURODEGENERATION AND COGNITIVE LOSS

STATEMENT OF GOVERNMENT FUNDING

The United States Government has a paid-up license in this invention and the right in limited circumstances to require the patent owner to license others in reasonable terms as provided for by the terms of NIH Grant No. R01 NS41783 awarded by the Department of Health and Human Services.

FIELD OF THE INVENTION

The present invention is directed to recombinantly engineered mice that are deficient in the production of presenilin and which exhibit an age-dependent progressive loss of cognitive function, synapses and neurons mimicking that seen in Alzheimer's disease. The invention includes methods of producing these mice and assays in which they may be used to identify agents that either accelerate or inhibit neurodegeneration.

BACKGROUND OF THE INVENTION

Alzheimer's disease is the fourth leading cause of death in the United States after heart disease, cancer and stroke. It is characterized by a progressive loss of cognitive function, neurodegeneration and an accumulation of amyloid plaques in the brains of patients. Although generally considered a disease of the elderly, an early onset familial form of Alzheimer's disease has been identified and associated with mutations in two genes, presenilin-1 and presenilin-2 (Sherrington, et al., *Nature* 375:754-760 (1995); Rogaev, et al., *Nature* 376:775-778 (1995); Levy-Lahad, et al., *Science* 269:970-973 (1995); Hiltunen, et al., *Eur. J. Hum. Genet.* 8:259-266 (2000); Jonghe, et al., *Hum. Mol. Genet.* 8:1529-1540 (1999); Tysoe, et al., *Am. J. Hum. Genet.* 62:70-76 (1998); Crook, et al., *Nat. Med.* 4:452-455 (1998)). In general, it is believed that mutations in these genes lead to an increase in the formation and aggregation of amyloid protein which, in turn, causes neuronal disruption and death (Duff, et al., *Nature* 383:710-713 (1996); Scheuner, et al., *Nature Med.* 2:864-870 (1996); Borchelt, et al., *Neuron* 17:1005-1013 (1996)). While this prevailing view posits that pathogenic presenilin mutations cause Alzheimer's disease via a toxic gain-of-function mechanism, it remains possible that such mutations may confer a partial loss of presenilin function.

Previous studies conducted on PS1−/− mice revealed an essential role for PS1 in neurogenesis and cortical development, but mutant mice displayed perinatal lethality due to skeletal defects (Shen, et al., *Cell* 89:629-639 (1997)). Although PS2−/− mice are viable and phenotypically normal (Donoviel, et al., *Genes & Dev.* 13:2801-2810 (1999); Herreman, et al., *Proc. Natl. Acad. Sci. USA* 96:11872-11877 (1999); Steiner, et al., *J. Biol. Chem.* 274:28669-28673 (1999)), mice that lack both presenilins (PS−/−) exhibit early embryonic lethality and severe early patterning defects indicating functional redundancy between PS1 and PS2 (Donoviel, et al., *Genes & Dev.* 13:2801-2810 (1999)).

In order to circumvent the early demise of PS1−/− mice, the Cre/loxP recombination system has been used to generate conditional knockout (cKO) mice in which the expression of PS1 is selectively eliminated in excitatory neurons of the forebrain beginning about at postnatal day 18 (Yu, et al., *Neuron* 31:713-726 (2001)). In contrast to the striking brain phenotypes observed in PS1−/− mice, PS1 cKO mice were found to exhibit only a subtle deficit in spatial memory, whereas synaptic transmission and plasticity are normal. Thus, the mice do not exhibit the broad range of progressive cognitive impairments characteristic of Alzheimer's disease. One possibility for these results is that presenilin-2 may be largely compensating for the deficiency in presenilin-1 activity and thereby masking a causal relationship between a loss of presenilin function and the development of age-dependent neuronal degeneration.

SUMMARY OF THE INVENTION

The present invention is based upon the discovery that mice engineered to be deficient in the production of both presenilin-1 and presenilin-2 in the adult brain exhibit an age-dependent deterioration of cognitive function and neurodegeneration that closely resembles that seen in Alzheimer's disease. Surprisingly, these mice do not exhibit an accumulation of the amyloid plaques which are generally believed to be responsible for neuronal degeneration in Alzheimer's patients.

In its first aspect, the invention is directed to a method for producing a presenilin-deficient mouse that can serve as a model of age-related neurodegeneration. This is accomplished by making a first recombinantly engineered mouse whose genomic DNA has a presenilin-1 gene with one or more exons flanked by loxP elements in such a manner that, when exposed to Cre, the exons are excised. The most preferred sites for the insertion of loxP elements are introns 1 and 3 of the presenilin-1 gene. In one especially preferred embodiment, one loxP element is inserted into intron 1, and another loxP site into intron 3. The genomic DNA of the mouse also includes one or more elements coding for Cre recombinase under the control of a promoter that is capable of acting in neurons, preferably the CaM kinase II promoter.

The method for producing presenilin deficient mice also requires the making of a second recombinant mouse. In this case, the mouse is engineered so that its genomic DNA has a presenilin-2 gene in which one or more exons, e.g, exon 5, have been interrupted by the introduction of an exogenous sequence (i.e., a sequence not normally found within the presenilin-2 gene) preventing the making of a functional protein.

The final step in the process is to crossbreed the first and second recombinantly engineered mice. Progeny may then be selected whose genomic DNA includes the loxP elements, the Cre coding sequence under the control of the promoter and a presenilin-2 gene in which at least one exon, preferably exon 5, is interrupted with an inactivating sequence.

Although the above method represents the preferred method for making presenilin deficient mice, other procedures may also be used. For example, other methods of genetic engineering may be employed to produce mice with reductions in presenilin activity in the adult brain. For example, other site-specific recombination systems, such as the FLP/FRT system, may be used in a manner similar to the Cre/loxP methodology to inactivate presenilin-1 conditionally. Alternatively, conditional or inducible expression of a dominant-negative presenilin-1 transgene (Wolfe, et al., *Nature* 398:513-7 (1999)) may also be used to reduce presenilin-1 function in the adult brain. A third possible genetic method involves the use of RNA interference (Elbashir, et al., *Genes Dev.* 15:188-200 (2001); *Nature* 411:

494-8 (2001)), either through introduction of interfering RNAs directly into the brain or the production of transgenic mice expressing interfering RNAs, or alternatively the use of anti-sense oligonucleotides introduced into the brain, to inhibit presenilin function. Such presenilin-1 mutant mice could then be crossed to the same presenilin-2 knockout mice described above to result in mice deficient in both presenilins in the adult brain.

Nongenetic methods can also be used to make presenilin deficient mice. For example, transduction of cell permeable proteins (Jo, et al., *Nat Biotechnol.* 19:929-33 (2001)) into the adult brain can be used to inhibit presenilin function. Alternatively, pharmacologic approaches based on peptide or small molecule inhibitors may be adopted. For example, Li et al. (*Nature* 405:689-694 (2000)) and others have described chemical compounds ("gamma-secretase inhibitors") that bind specifically to presenilin-1 and presenilin-2 and inhibit their activity. These, or similar compounds, can be administered to mice or other animals to make them presenilin deficient. The animals can then be used in the same way as the genetically engineered mice described herein. One advantage of using chemical compounds is that administration can be conveniently started and stopped at defined times by experimenters based upon their objectives.

In another aspect, the invention is directed to a presenilin-deficient mouse which can serve as a model of age-related neurodegeneration and cognitive loss. The mouse is viable (i.e., capable of surviving) for at least 6 months and preferably 12-16 months after birth, and produces normal amounts of presenilins during embryonic development and the first 2-4 weeks after birth. The most preferred embodiment of this invention is directed to mice in which a loxP element has been introduced into intron 1 of presenilin-1 and another loxP element has been introduced into intron 3. The mice should also include within their genome a coding sequence for Cre recombinase which is under the control of a promoter active in neurons (preferably the CaM kinase II promoter) and presenilin-2 genes that have been inactivated by the introduction of an exogenous sequence into an exon (e.g., exon 5). Other embodiments of this invention which can serve as a model for age-related neurodegeneration and cognitive loss are described above.

The invention also includes methods of assaying a test compound for its ability to affect age-related neurodegeneration and cognitive loss. This is accomplished by administering the test compound to any of the presenilin-deficient mice described above. After a period of time, e.g., one or more months, the mice are examined to determine their cognitive ability along with similar presenilin deficient control animals not receiving test compound. If desired, normal mice, i.e., mice not engineered to reduce presenilin production, may also be included in assays to aid in comparisons. Mice should preferably be tested at several intervals, for example at two months, six month and nine months of age, and test compound should preferably be administered in a range of doses (e.g. from 1 µg-10 mg per day). Mice can be assessed for cognitive function using either the tests described herein or similar tests known in the art. Based upon the results, a conclusion can then be reached as to the effectiveness of the test compound in either retarding or promoting neurodegeneration. Compounds that slow the loss of cognitive function have potential as therapeutic agents. Compounds that accelerate loss may constitute environmental or dietary factors that contribute to disease progression and that should be avoided by patients.

Based upon the results described herein, it may be concluded that decreased presenilin activity can produce effects that are similar to those seen in Alzheimer's patients. As a first corollary, the concept has developed that diagnostic methods for an age-related neurodegenerative disease, such as Alzheimer's disease, may be based on the level of presenilin activity in a subject as reflected in total presenilin protein, mRNA or enzymatic activity. For example, if the total presenilin protein (i.e. presenilin-1+presenilin-2) is significantly lower (e.g., lower by 15% or more) relative to that seen in individuals known to be disease free or in the population at large, this is an indication that the subject may develop an age-related neurodegenerative disease, e.g., Alzheimer's disease. Similar considerations apply with respect to total presenilin mRNA and total presenilin enzymatic activity. Any of the methods for assessing these levels that are known in the art may be used. The biological samples used may be cerebrospinal fluid, neural tissue or neurons. Other biomarkers (e.g., the accumulation of presenilin substrates) that reflect reduced presenilin activity in the adult brain may also be used. The invention is thus directed in an additional aspect to a method for diagnosing Alzheimer's disease by detection of reduced presenilin function.

As a second corollary, the concept has developed that increasing presenilin activity may be used to retard disease progression. Thus, in another aspect, the invention is directed to a method of treating a patient for neurodegeneration and cognitive loss such as that seen in Alzheimer's patients by increasing presenilin activity in neural tissue. This may be accomplished by several possible methods. For example, one or both presenilins may be administered to a patient at a therapeutically effective dose using an appropriate delivery mechanism. For the purposes of the present invention, a "therapeutically effective dose" is defined as sufficient presenilin-1 or presenilin-2 to slow the rate of neurodegeneration and/or cognitive decline as measured by either tests of cognitive function or other clinical diagnostic tests. Similarly, "an appropriate delivery mechanism" is defined as a route or method of administration by which presenilins may be introduced in a functional state into neurons in appropriate brain regions. Such routes or methods of administration may include modification of presenilin proteins so as to render them cell permeable, application of presenilin proteins to the cerebrospinal fluid, or introduction of nucleic acid constructs to produce presenilins (presenilin "gene therapy"). For example, patients may be treated by administering a polynucleotide comprising a sequence encoding either presenilin-1 or presenilin-2 operably linked to a promoter active in neurons. As used herein, the term "operably linked" indicates that the transcription of the sequence encoding either presenilin-1 or presenilin-2 is under the control of the promoter and that protein having the correct amino acid sequence is eventually produced. Sufficient polynucleotide should be administered to the cerebrospinal fluid for it to be taken up and expressed by neurons at a level sufficient to slow the rate of neurodegeneration and/or cognitive loss as measured by either tests of cognitive function or clinical diagnostic tests. Methods for the in vivo delivery of nucleic acids are well known in the art and may involve the use of viral vectors (adenoviral vectors), chemical agents promoting in vivo cell transformation (e.g., liposomes), or the direct administration of naked DNA. Alternatively, cells may be removed from a patient, transformed and then reimplanted. As an alternative approach to the augmentation of presenilin function, patients may be treated with compounds that enhance endogenous presenilin function, obviating the need for the introduction of exogenous sources of presenilin. Such compounds may be identified through assays in cultured neurons and/or mice.

BRIEF DESCRIPTION OF THE DRAWINGS

FIG. 1: Generation of a floxed PS1 allele. FIG. 1 shows the targeting strategy and restriction map of the locus used in producing PS-1 conditional knockout mice. The PS1 exons 2 and 3, are flanked with a loxP site and the floxed CMV-HYG/TK selection cassette. The loxP1 site and the floxed selection cassette were inserted in PS1 introns 1 and 3, located 340 bp upstream of and 360 bp downstream of the intron/exon boundaries, respectively. The loxP sites are indicated as arrowheads. Multiple Xmn I sites are present in the locus, but only the relevant one is shown. The loxP1 site and the floxed selection cassette are not drawn to scale. P1 and P4 are primers specific for loxP1 used for cloning and PCR. P3, P5 and P2 are PCR primers specific for PS1 intron 1, exon 3 and intron 3, respectively. 5' and 3' probes are 0.5 and 0.7 kb fragments used for screening homologous recombinants, and are located outside of the 5' and 3' homologous regions.

DETAILED DESCRIPTION OF THE INVENTION

The present invention is directed to a mouse model of age-dependent cognitive impairment and neurodegeneration. Mice are produced by incorporating genomic mutations that eliminate the ability of animals to make presenilin-1 and presenilin-2. Compared to their unmodified counterparts, the mice show a progressive loss of cognitive ability, including a decrease in memory, progressive impairment of synaptic function, and, importantly, progressive neurodegeneration. Although these mice exhibit the basic characteristics of Alzheimer's disease, they do not accumulate amyloid plaques in brain tissue. This suggests that, contrary to accepted dogma, Alzheimer's disease may, at least in some instances, be caused by factors independent of the accumulation of amyloid-related peptides.

A. Making of Viable Presenilin-1 Deficient Mice

The most preferred method of making presenilin-deficient mice involves first producing viable animals deficient in presenilin-1. However, presenilin-1 appears to be necessary for normal fetal development and a simply introducing disrupting sequences into presenilin-1 exons by homologous recombination will result in animals that die before they can be adequately studied or pass on their mutations on to offspring. Therefore, a strategy must be used in which the presenilin-1 gene is active during the early stages of development and subsequently lost. One way to achieve this is using the Cre/loxP system described in U.S. Pat No. 4,959, 317. By linking the Cre recombinase to the CaM kinase II promoter, and introducing this into the mice genome, expression of Cre is delayed until approximately 2-3 weeks after birth. This allows sufficient time for normal embryonic development.

Figure 1:
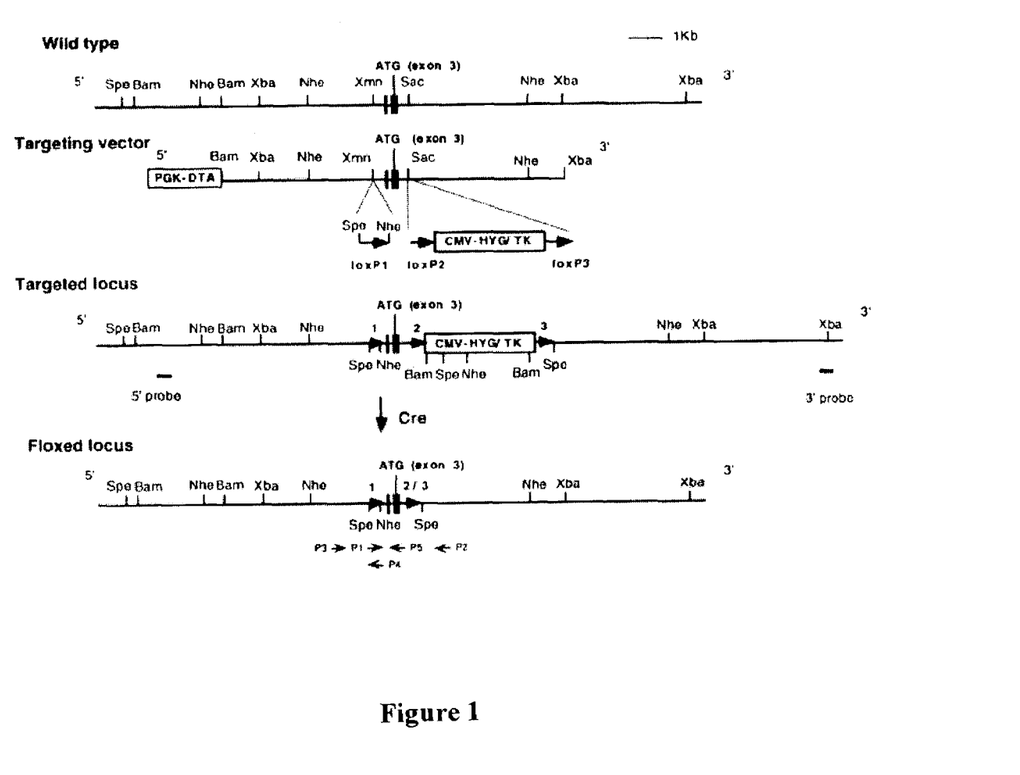

The loxP elements should be incorporated into the mouse genomic DNA at positions that do not interfere with normal expression, but which result in the elimination of exons critical for function upon exposure to Cre. As discussed in detail in the Examples section below, this may be accomplished by introducing loxP elements into intron 1 and intron 3 of presenilin-1. In order to aid in the selection of cells that have undergone desired recombination, targeting vectors carrying the loxP elements may also include marker genes, e.g., genes for hygromycin resistance and for thymidine kinase. The marker genes may be flanked by loxP elements as discussed in Example 1. Sequences for the presenilin-1 gene have been described by Sherrington, el al. (*Nature* 375:754-760 (1995)) and a strategy for targeting presenilin-1 is shown in FIG. 1.

B. Making of Presenilin-2 Knockout Mice

Although presenilin-2 probably performs biological functions that are very similar to presenilin-1, the expression of the presenilin-2 gene can be completely eliminated in mice without destroying viability or affecting normal development and function. Thus, standard procedures for producing "knockout" mice by homologous recombination can be employed to make presenilin-2 deficient mice. One preferred method for making presenilin-2 mice has been reported in *J. Biol. Chem.* 274:28669-28673 (1999).

In general, DNA constructs used in making these mice will contain two relatively long (greater than 1 Kb) targeting segments that are identical to the endogenous gene sequence for presenilin-2, and a non-homologous sequence which codes for drug resistance, e.g., neomycin resistance. Procedures for producing appropriate targeting vectors and for carrying out homologous recombination have been described in detail in the literature (see, e.g., Capecchi, *TIG* 5:70 (1989); Mansour, et al., *Nature* 336:348 (1988); Thomas, et al., *Cell* 51:503 (1987); and Doetschman, et al., *Nature* 330:576 (1987); see, also, Sambrook, et al., *Molecular Cloning: A Laboratory Manual*, Cold Spring Harbor Laboratory Press, Cold Spring Harbor, N.Y. (1989)).

In order to incorporate a marker sequence into the targeting segment for presenilin-2, the DNA can be digested with one or more restriction enzymes selected to cut at specific locations. These may be identified using the sequence information for presenilin-2 which has been previously reported in the art (see Rogaev, et al., *Nature* 376:775-778 (1995); Levy-Lahad, et al., *Science* 269:970-973 (1995)). Any location which results in the elimination of a functional gene product after homologous recombination may be used. As discussed in Example 2 below, disruption of exon 5 will fulfill this requirement, but it is expected that the disruption of other exons should work equally well.

The marker sequence will typically be an antibiotic resistance gene or other gene whose expression can be easily detected and which is not normally present in the host. The marker gene may be expressed in the host cell either as a result of its being operably linked to a promoter in the construct or by coming under the control of the native presenilin-2 promoter as a result of homologous recombination. In cases where it is part of the construct, the promoter should be selected based upon its having a high activity in mouse embryonic stem cells, e.g., the CMV promoter may be used. The most preferred gene for use as a marker is the neomycin resistance gene (Neo). Cells which have integrated Neo into their genome and which are expressing this gene are resistant to G418 and this provides a simple means for selecting recombinant cells.

DNA constructs may be either circular or linear. However, it is generally preferred that, prior to introduction into mouse embryonic stem cells ("ES cells"), circular constructs be linearized. ES cells should be selected based upon their ability to integrate into and become part of the germ line of a developing embryo. Any ES cell line that has this characteristic may be used, e.g., the murine cell line D3 (ATCC, 12301 Parklawn Drive, Rockville, MD, Catalog No. CRL1934). After appropriate cells have been chosen, they are cultured and prepared for DNA insertion using methods well known in the art (see, e.g., Robertson, in: *Teratocarcinomas and Embryonic Stem Cells: A Practical Approach*, E. J. Robertson, ed., I.R.L. (1986); and Hogan, et al., *Manipulating the Mouse Embryo: A Laboratory Manual*, Cold Spring Harbor Laboratory Press, Cold Spring Harbor, N.Y. (1986)). The introduction of the presenilin-2 constructs into host cells can be accomplished using any of a variety of methods such as electroporation, microinjection or calcium phosphate treatment. The preferred method of insertion is by electroporation.

Screening of transfected cells can be carried out using several different methods. In cases where an antibiotic resistance gene has been used as a marker, cells can be cultured in the presence of antibiotic to identify recombinants. In cases where other types of markers are used, Southern hybridizations may be carried out using labeled probes specific for the marker sequence. Finally, if the marker gene encodes an enzyme whose activity can be detected (e.g., beta-galactosidase), enzymatic assays can be performed. It will usually be desirable not only to identify cells in which recombination has occurred, but also to ensure that specific recombination, i.e., integration at the presenilin-2 gene locus, has occurred. To identify cells which have undergone integration at the proper site, chromosomal DNA can be extracted from cells using standard methods and Southern hybridizations can be performed using probes designed to hybridize specifically to DNA derived from targeting constructs. Alternatively, PCR amplification can be performed using primers that will only act in cells where homologous recombination has occurred at the presenilin-2 locus or which produce a distinctive product of known size from such cells.

Once engineered ES cells have been produced, they may be used to make knockout animals that are deficient in the production of presenilin-2. The first step in this procedure involves incorporating the mutant cells into an embryo. The preferred method for accomplishing this is by microinjection into an embryo at the blastocyst stage of development. In mice, blastocysts at about 3.5 days of development may be obtained by perfusing the uterus of pregnant animals (see Bradley, in: *Teratocarcinomas and Embryonic Stem Cells: A Practical Approach*, Robertson, IRL Press, Washington, D.C. (1987)). Preferred blastocysts are male and have genes coding for coat color or another phenotypic marker that is different from the corresponding marker encoded by the stem cell genes. In this way, offspring are produced that can be easily screened for the presence of a mutant presenilin-2 allele. For example, if the ES cell line carries the gene for a white coat, the embryo selected will, preferably, carry the gene for a black or brown coat and offspring carrying a mutant presenilin-2 allele should have mosaic coats.

After the ES cells have been incorporated into the blastocyst, the chimeric embryo is implanted into the uterus of a pseudopregnant animal. Such animals may be prepared by mating females with vasectomized males of the same species. The pseudopregnant stage of the female is important for successful implantation and, typically, female mice about 2 or 3 days pseudopregnant should be used.

After chimeric embryos have been implanted into pseudopregnant animals, they are allowed to develop to term and offspring are then screened for the presence of a mutant presenilin-2 allele. In cases where a phenotype selection strategy has been employed, e.g., based upon coat color as described above, initial screening may be accomplished by simple inspection of animals. In addition, chromosomal DNA may be obtained from the tissue of offspring, e.g., from tail tissue, and screened for the presence of a modified nucleotide sequence at the presenilin-2 gene locus using Southern blots and/or PCR amplification. Once offspring have been identified carrying the presenilin-2 gene mutation, they can be interbred to produce homozygous animals characterized by the impaired synthesis of functional presenilin-2.

As discussed above, heterozygotes may be identified using Southern blots or PCR amplification. Homozygotes may be identified by Southern blotting of equivalent amounts of genomic DNA obtained from the offspring of crossed heterozygotes, from the heterozygotes themselves, and from wild-type animals. Probes should be designed to bind to a portion of the presenilin-2 gene present in all animals and the presence of mutant alleles can be determined by the relative position of bands in autoradiographs. Alternatively, analysis may be performed based upon the relative sizes of PCR amplification products.

Other means for identifying and characterizing transgenic animals are also available. For example, Northern blots can be used to probe mRNA obtained from tissues of offspring animals for the presence or absence of transcripts encoding either presenilin-2, the marker gene product, or both. In addition, Western blots might be used to assess presenilin-2 expression by probing with antibody specific for this protein.

C. The Making and Use of Mice Deficient in Presenilin 1 and Presenilin 2

Once viable presenilin-1 deficient mice have been obtained using the Cre/loxP procedure described above, they may be crossed with the presenilin-2 knockout mice to make animals that are entirely deficient with respect to presenilin production. This procedure is discussed in Example 3 below. As described therein, the presenilin deficient animals undergo normal development but exhibit a progressive decline in cognitive function which may be measured by a variety of specific assays, such as "open field" assays, "rotarod" assays, "water maze" assays, fear conditioning assays, etc. Any or all of these may be used in determining the cognitive ability of animals. It is also expected that similar assays should work equally well.

Although the presenilin-deficient animals described above may be used in basic experiments for studying the progression of neurodegenerative diseases, it is expected that they will be especially valuable in helping to identify therapeutic agents that slow the degenerative process. In order to identify such agents, a comparison may be made between normal animals, animals that are presenilin deficient, and animals that are presenilin deficient but which have been administered a test compound. Typically, test compound administration should be maintained over an extended period of time, at least one month, and animals should be assessed for cognitive ability at several different times, e.g., at 2 months, 6 months and 9 months after birth. The initiation of test compound administration can be started at any point in the aging process. For example, administration could be started soon after birth in order to determine whether the test compound is effective in relatively normal animals in helping prevent the initiation of neurodegeneration, or, alternatively, the test compound may be given after cognitive impairment is observed to determine its effect in slowing the process once it has begun. In addition to. being useful in identifying agents that slow the degenerative process, it is expected that the mice will also be useful in identifying agents that cause it to accelerate. Thus, assays may be helpful in determining whether specific environmental factors contribute to the development of neurodegenerative disorders.

D. Therapeutic Methods

Therapeutic methods may involve either the administration of polypeptide or the administration of nucleic acids that encode the polypeptide. In the latter case, oligonucleotides designed for the expression of either presenilin-1 or presenilin-2 may be administered directly to patients or, alternatively, cells from patients may be removed, transfected and then reimplanted. The in vivo transfection of cells has been known for many years and may be accomplished using viral vectors (see e.g. U.S. Pat. No. 6,020,191); liposomes (see e.g., Nicolau, *Meth. Enzymol.* 149:157-176 (1987)); DNA complexed to agents that facilitate cellular uptake (see e.g., U.S. Pat. No. 5,264,618; WO 98/14431); or even by simply injecting naked DNA (see e.g., U.S. Pat. No. 5,693,622). Administration may be repeated as is necessary until a positive therapeutic effect is observed. For example, DNA may be repeatedly administered to a patient until neurodegeneration is retarded. Dosages, the scheduling of administration and the evaluation of patient response may be carried out and optimized using procedures well known in the area of clinical medicine.

Presenilin proteins or polynucleotides may be administered in either a single or multiple dosage regimen and may be given either alone or in conjunction with other therapeutic agents. Compositions for injection, preferably into cerebrospinal fluid, may be made using conventional techniques and may include isotonic saline, water, polyglycols, Ringer's solution, etc. All dosage forms may be prepared using methods that are standard in the art (see e.g., *Remington's Pharmaceutical Sciences*, 16 edition, A. Oslo editor, Easton, Pa. (1980)).

EXAMPLES

Example 1

Making of Mice with Floxed Presenilin-1

The procedure for making conditional knockout mice in which introns 1 and 3 are engineered to incorporate loxP elements has been described in previous references (Yu, et al., *Genesis* 26:5-8 (2000); Yu, et al. *Neuron* 31:713-726 (2001)). Methods for obtaining the mouse PS-1 gene as well as its sequence have also been described (Sherrington, et al., *Nature* 375:754-760 (1995)).

In order to generate a floxed presenilin-1 (PS1) allele, a targeting vector corresponding to the mouse genomic sequence containing exons 1 and 2 of the PS-1 gene was obtained and engineered to incorporate three loxP elements. The targeting vector (FIG. 1) contains a loxP site flanked by Spe I and Nhe I restriction sites in PS1 intron 1 (loxP1) and a floxed positive and negative selection cassette (CMV-HYG/TK) in PS1 intron 3 (loxP2 and loxP3). The cassette encodes a fusion protein with hygromycin-resistance (HYG) and thymidine kinase (TK) activities under the control of the CMV promoter. Another negative selection cassette (PGK-DTA), which encodes diphtheria toxin under the control of the phosphoglycerate kinase promoter (PGK), was included in the targeting construct to allow enrichment for the correctly targeted embryonic stem (ES) cell clones (Soriano, *Development* 124:2691-700 (1997)).

The 46-mer P1 and P4 containing Spe I, loxP, and Nhe I sites were annealed and inserted into the Xmn I site of PS1 intron 1. The floxed CMV-HYG/TK cassette was inserted into the Sac I site of PS1 intron 3. The targeting vector was thoroughly examined with over 10 single and double restriction digestions. It was further verified by sequencing the floxed region, all three loxP sites, and adjacent regions. The sequences of the PCR primers are as follows:

P1: 5' ACTAGTATAACTTCGTATAATGTATGCTAT (SEQ ID NO:1)
    ACGAAGTTATGCTAGC;

P2, 5' GGTTTCCCTCCATCTTGGTTG;        (SEQ ID NO:2)

P3, 5' TCAACTCCTCCAGAGTCAGG;         (SEQ ID NO:3)

P4, 5' GCTAGCATAACTTCGTATAGCATACATTAT (SEQ ID NO:4)
    ACGAAGTTATACTAGT;

P5, 5' TCTGGAAGTAGGACAAAGGTG.        (SEQ ID NO:5)

The linearized targeting vector was transfected into J1 ES cells by electroporation. In the presence of the positive selection drug, hygromycin B, only those clones in which the CMV-HYG/TK selection cassette has been integrated and the PGK-DTA cassette has been removed by homologous recombination survive. After selection in hygromycin-containing medium (120 mg/ml) for 7.5 days, 192 of these ES cell clones were picked and expanded.

It is important to distinguish ES cells that have undergone homologous recombination in the 5' homologous region from those undergoing homologous recombination within the floxed region, which results in exclusion of loxP1. Genomic DNA derived from 96 individual ES cell clones was subjected to Spe I digestion followed by hybridization with the 5' probe. Southern analysis showed that 7 ES cell clones underwent targeting events in the 5' homologous region ($\approx$5 kb), and 8 clones exhibited targeting events in the floxed region ($\approx$1 kb). Interestingly, the frequency of homologous recombination within the floxed region appears similar to that within the 5' region, despite its much smaller size. In addition, the use of the negative selection cassette PGK-DTA markedly increased the targeting frequency ($\approx$75-fold), compared to disruption of the PS1 locus using the same homologous regions but un the absence of the cassette.

These 15 ES cell clones were expanded, and their genomic DNA was digested with Spe I and BamHI followed by hybridization with the 5' and 3' probes, respectively. Seven of the twenty remaining negative clones were analyzed by PCR using P3 and P2 for recombination between loxP1 and loxP3. All 20 tested clones yielded a 376 bp product that was not observed in the parent clones B37 and B38, indicating excision of the entire floxed region. This result also indicates a high efficiency of negative selection, most likely due to low plating density. Surprisingly, the 376 bp product was also detected in the five positive clones, suggesting mixed populations of ES cells carrying loxP1/3 and loxP2/3 recombination events. These five clones were further tested by Southern analysis using Nhe I and Spe I digestion followed by hybridization with a probe specific for PS1 exons 2 and 3. In addition to a 7 kb Nhe I fragment representing the wild-type PS1 locus, a 4.5 kb Two of the confirmed ES cell clones (B37-16 and B38-9) containing higher percentages of the correctly recombined ES cells (loxP1, 2/3) were injected into C57BL/6J and Balb/c mouse blastocysts. Sixteen and five chimeric mice were obtained from the B37-16 and B38-9 clones, respectively. The chimeras were then mated to C57BL/6 mice to obtain heterozygous floxed F1 mice. Genotyping of 247 F1 mice by PCR and Southern analysis showed that only 26 of them carried the properly recombined floxed PS1 locus with loxP1 and 2/3, whereas 46 carried the loxP1/3 locus. This result is consistent with the heterogeneity of these two ES cell populations in B37-16 and B38-9 clones. The 26 heterozygous floxed F1 mice were derived from two B37-16 and one B38-9 chimeras.

Example 2

Making of Presenilin-2 Knockout Mice

Standard procedures for making transgenic animals have been described in the art and may be applied to the making of animals which are deficient in the production of PS-2 (see Capecchi, M. *TIG* 5:70 (1989); Mansour, et al., *Nature* 336:348 (1988); Thomas, et al., *Cell* 51:503 (1987); and Doetschman, et al., *Nature* 330:576 (1987)). The full length sequence of the mouse presenilin-2 gene has been previously described (Rogaev, et al., *Nature* 376:775-778 (1995); Levy-Lahad, et al., *Science* 269:970-973 (1995)). A targeting vector is constructed with a sequence corresponding to the gene but in which exon 5 is interrupted with a marker sequence coding for a neomycin resistance gene and a HSV-thymidine kinase gene. This is introduced into mouse embryonic stem cells for the purpose of integrating the fragment into the mouse genome at the PS-2 gene locus. The recombinant stem cells so produced are selected and then incorporated into a mouse blastocyst to form a chimeric embryo. This is implanted into a pseudopregnant mouse and allowed to develop into a viable offspring.

The offspring produced using the procedures described above, are screened to identify heterozygous mice containing a mutant PS-2 gene allele. These mice are then bred to develop homozygous transgenic mice having a phenotype characterized by the substantial absence of fully presenilin-2.

Example 3

Mouse Model of Age-Dependent Neurodegeneration

In the present example, we cross PS1 cKO mice into the PS2-null background to generate viable conditional double KO (PS cDKO) mice lacking both PS in the postnatal forebrain. We found that PS cDKO exhibit hippocampal memory and synaptic plasticity impairments prior to neuropathological changes, indicating a novel role for PS in synaptic function. Strikingly, these cDKO mice subsequently develop synaptic, dendritic and neuronal degeneration with accompanying astrogliosis in an age-dependent manner, demonstrating an essential role for PS in maintaining neuronal integrity and survival.

A. Materials and Methods

Mice

The generation of PS1 cKO and PS2-/- were described previously (Steiner, el al., *J. Biol. Chem.* 274:28669-28673 (1999); Yu, et al., *Neuron* 31:713-726 (2001)). PS cDKO mice were generated by crossing PS1 cKO (fPS1/fPS1; CaM-Cre) and fPS1/fPS1 with PS2-/- to obtain fPS1/+; PS2+/-; CaM-Cre and fPS1/+; PS2+/- mice, respectively. fPS1/+; PS2+/- mice were bred together to obtain fPS1/fPS1; PS2-/-, which were then bred with fPS1/+; PS2+/-; CaMCre to obtain cDKO mice (fPS1/fPS1; PS2-/-; CaM-Cre). All four experimental genotypic groups (fPS1/fPS1; CaM-Cre; PS2-/-, fPS1/fPS1; CaM-Cre, fPS1/fPS1; PS2-/- and fPS1/fPS1) were obtained from two crosses (fPS1/fPS1; PS2-/-; CaM-Cre×fPS1/fPS1; PS2-/- and fPS1/fPS1; CaMCre×fPS1/fPS1), and littermates were used for all experiments. fPS1/fPS1 and PS2-/- mice were generated in C57BL6/129 hybrid background, whereas CaM-Cre transgenic mice were generated in C57BL6/CBA hybrid strain and then backcrossed to B6 for more than 10 generations. Therefore, the genetic background of all experimental groups is C57BL6/129 hybrid.

All mice were housed in a standard 12-hour light-dark cycle. The experimenters of behavioral, electrophysiological and morphological studies were all blind to the genotypes of the mice.

Preparation of Brain Sections and Immunostaining

Brains were perfused with PBS, fixed in 10% formalin, processed for paraffin embedding and serially sectioned (10 µm). Saggital brain sections were deparaffinized, alcohol dehydrated and stained with 0.5% cresyl violet (Niss1) or immunostained with monoclonal antibodies raised against MAP2 (1:200; Sigma), synaptophysin (1:200; Sigma) and GFAP (1:500; Sigma), and incubated with either Alexa Fluor 488 goat anti-mouse or Alexa Fluor 594 goat anti-mouse secondary antibodies (Molecular Probes), and then analyzed with a Zeiss 510 confocal laser scanning microscope.

Stereological Neuronal Count

Neuron counts were performed using the optical dissector technique in 10 µm paraffin saggital sections stained with cresyl violet. Neuronal number and volume of the neocortex were determined as described in (Irizarry, el al., *J. Neuropath. Exp. Neurol.* 56:173-177 (1997)). Serial sections spaced 400 µm apart through the entire neocortex of the left hemisphere of 3-5 mice per genotype were counted. The number of neurons in the neocortex of each brain section was determined by a systematically random sampling using a 50×50 µm-counting box. Under a100× water objective, cells with a typical neuronal morphology and clear nucleolus were counted if they were not present in the initial plane of focus, but came into focus as the optical plane moved into the brain section. The estimation of the number of neurons was calculated by multiplying the neuronal density of the counted area by the volume of the neocortex. One-way ANOVA was used to assess statistical significance.

Open Field

Individual mice were placed in 42 cm×42 cm acrylic animal cages for 15 min following which they were returned to their home cages. Their horizontal and vertical movements were continuously recorded by 3 arrays of 16 infrared light beam sensors (AccuScan Instruments, Columbus, Ohio). Beam breaks were converted to variables such as horizontal and vertical activity and total distance traveled using AccuScan VersaMax software.

Rotarod

Mice were placed 4 at a time on an Economex Accelerating Rotarod for mice (Columbus Instruments) equipped with individual times for each mouse. Mice were initially trained to stay on the rod at a constant rotation speed of 5 rpm. After a 2 min rest, mice that would fall were placed back on the rotarod until they were able to continuously stay on the rotating rod for 2 min. Following training, mice were subsequently tested by placing them on the rod at a rotation speed of 5 rpm. The latency to fall as the rod accelerated by 0.2 rpm per second was measured. Mice were allowed to rest for 2 min after the last mouse fell. This procedure was repeated for a total of 3 trials, and then the mice were returned to home cages.

Water Maze

The water maze is a circular pool 160 cm in diameter. During the hidden platform test, the platform (10 cm in diameter) was kept submerged under water and maintained in the same position. Each mouse was given either 4 trials daily for 13 days or 6 trials daily (2 trials per block, ~2 hr inter-block interval) for 5 days. During the 60-second training period, if the mice were unable to locate the hidden platform, they were guided to the platform by hand and allowed to remain on it for 30 seconds. The movement of the mice was monitored using an automated tracking system (HVS Image). Following training days 3 and 5 (5-day training), mice were subjected to a 60-second probe trial in which the platform was removed and the mice were allowed to search for it. In the visible platform test, extra-maze distal cues were removed, and the platform was raised above water and marked by a black and white golf ball. The intensive training eliminated subtle memory defects we previously observed in PS1 cKO mice using a more difficult training protocol.

Contextual Fear Conditioning

On training day, mice were placed within the conditioning chamber for 3 minutes before the onset of the US (footshock). Following a 1-sec-1 mA single footshock they were allowed to remain in the chamber for additional 2 minutes and then returned to their home cages. Mice were tested 24 hours following training for 4 minutes in the same conditioning chamber. Mice from all genotype groups responded to the foot shock similarly by jumping and vocalization. Freezing was defined as a complete cessation of movement except for respiration and scored by an automated system (Actimetrics). Using this protocol, younger mice routinely show lower levels of freezing response than older mice.

Electrophysiology

Acute hippocampal slices (400 μm) were maintained in an interface storage chamber containing artificial cerebrospinal fluid (ACSF: 124 mM NaCl, 5 mM KCl, 1.25 mM $NaH_2PO_4$, 3 mM $MgCl_2$, 1 mM $CaCl_2$, 26 mM $NaHCO_3$, 10 mM dextrose, pH 7.4) at 30° C. as described (Yu, et al., *Neuron* 31:713-726 (2001)). Stimulation (200 μs) pulses were delivered with a bipolar concentric metal electrode. Synaptic strength was quantified as the initial slope of field potentials recorded with ACSF filled microelectrodes (1 to 2 MΩ). Baseline responses were collected at 0.07 Hz with a stimulation intensity that yielded a half-maximal response. LTP was induced by five episodes of theta burst stimulation (TBS) delivered at 0.1 Hz. Each episode contains ten stimulus trains delivered at 5 Hz and each train consisted of four pulses at 100 Hz. Average responses (mean+SEM) are expressed as percent of pre-TBS baseline response (at least 10 min of stable responses). LTD was induced with 900 paired-pulses (40 ms apart) delivered at 1 Hz. A repeated measures ANOVA and nonpaired t test were used to assess statistical significance.

ELISA

Levels of mouse endogenous Aβ peptides in the cerebral cortex were measured by ELISA, as previously described (Johnson-Wood, et al., *Proc. Natl. Acad. Sci. USA* 94:1550-1555 (1997)). Monoclonal antibodies 2G3 and 21F12, specific for Aβ x-40 and Aβ x-42, respectively, were used as the capture antibodies. The biotinylated monoclonal 4G8 was used as the detection antibody. Streptavidin-conjugated alkaline phosphatase and AttoPhos (Amersham) were used as the reporter system. The cortex of APP−/− mice was used as negative control, and no Aβ peptides were detected.

Golgi Staining and Quantification of Dendritic Morphology

Brains of 4 cDKO and 3 control male mice at 9 months were dissected, processed for Golgi staining as described in (Vyas, et al., *J. Neurosci.* 22:6810-6818 (2002)), and serially sectioned (120 μm). 10 intact Golgi-impregnated pyramidal neurons per brain were selected for quantification of their dendritic length and branch points. Camera lucida tracings (500×) were obtained (Leitz Orthoplan) from selected neurons and scanned. One-way ANOVA was used to assess statistical significance.

B. Results

Normal Brain Morphology in PS cDKO Mice at 2 Months

In order to generate forebrain-specific PS conditional double knockout (PS cDKO) mice, we crossed floxed PS1 (fPS1), CaMKII-Cre transgenic (Yu, et al., *Neuron* 31:713-726 (2001)) and PS2−/− (Steiner, et al., *J. Biol. Chem.* 274:28669-28673 (1999)) mice together to obtain fPS1/fPS1; CaMKII-Cre; PS2−/− (cDKO) mice. Consistent with previous reports (Yu, et al., *Neuron* 31:713-726 (2001)), in situ hybridization and Western analyses confirmed progressive inactivation of PS1 and absence of PS2 in the cerebral cortex of cDKO mice. PS cDKO mice are viable and indistinguishable from littermate controls until the age of 7-9 months. Open field and rotarod tests of PS cDKO (n=10), PS1 cKO (n=10), PS2−/− (n=11) and control (n=10) mice at 2-3 months revealed no significant differences. By 7-9 months of age, however, cDKO mice are readily distinguishable from their littermates and exhibit excessive stereotyped grooming.

Nissl stained brain sections of cDKO, PS1 cKO, PS2−/− and control mice at 2 months revealed normal brain morphology. Stereological neuron counting showed no significant differences in neuronal number (p=0.97) and volume (p=0.42) in the neocortex of cDKO and control mice. Immunohistochemical analysis showed similar immunoreactivity for glial fibrillary acidic protein (GFAP), microtubule-associated protein 2 (MAP2) and synaptophysin in the neocortex and hippocampus of all four genotypes. These results indicated normal brain and neuronal morphology in cDKO mice at this age.

Mild Memory Impairment in PS cDKO Mice at 2 Months

To determine the functional effects of PS inactivation in the adult brain, we examined PS cDKO mice in the Morris water maze task (Morris, et al., *Nature* 297, 681-683 (1982)), a widely used behavioral paradigm for the assessment of hippocampal learning and memory. PS cDKO (n=18), PS1 cKO (n=11), PS2−/− (n=13) and control (n=17) mice were trained intensively with 6 trials per day (3 blocks of 2 trials) over 5 days to learn the position of a hidden escape platform in a circular pool using distal spatial cues. PS cDKO mice exhibited significantly longer latencies (p<0.001) and path lengths (p<0.0001) compared to the control, while the swimming speed was similar (p=0.23). In the post-training probe trial, all four genotypic groups searched preferentially in the target quadrant where the platform was previously located (T versus AL, AR or OP; p<0.0002). The total number of platform crossings by cDKO mice (2.4±0.5), however, was significantly lower than that of control (4.2±0.4), PS1 cKO (4.4±0.4) and PS2−/− (4.3±0.6) mice (p<0.0003). To determine whether the impairment exhibited by cDKO mice could be due to poor vision, motivation and/or sensorimotor abilities, all four genotypic groups were tested in the visible platform version of the task (4 trials per day for 5 days). All groups improved their performance rapidly with similarly low latencies (p>0.5). These results demonstrate that cDKO mice exhibit a mild impairment in spatial learning and memory, whereas PS1 cKO and PS2−/− mice performed as well as control mice.

We further assessed PS cDKO (n=25), PS1 cKO (n=19), PS2−/− (n=11) and control (n=23) mice at 2 months in contextual fear conditioning, in which robust memory can be acquired in a single training session (Phillips, et al., *Behavioral Neuroscience* 106:274-285 (1992)). Although all four genotypic groups displayed similar levels of freezing immediately after training (p>0.62), PS cDKO mice (16.7±2.8%) showed significantly reduced levels of freezing to the context 24 hours following training compared to control (27.4±3.7%), PS1 cKO (29.4±4.4%) and PS2−/− (34.3±7.7%) mice (p<0.01). These results show intact long-term contextual memory in PS1 cKO and PS2−/− mice but impaired long-term contextual memory in cDKO mice.

Impaired Synaptic Plasticity in PS cDKO Mice at 2 Months

The memory impairment exhibited by cDKO mice at 2 months prompted us to examine these mice for deficits in synaptic transmission and plasticity in the Schaeffer collateral pathway. We first quantified the initial slope of the evoked field excitatory postsynaptic potential (fEPSP) and the amplitude of the fiber volley (FV), which is a measure of the number of recruited axons, in acute hippocampal slices. In cDKO mice the maximal fEPSP (2.86±0.21 V/sec) and FV were normal (0.59±0.07 mV) compared to control mice (2.50±0.21 V/sec, p=0.46 for fEPSP; 0.52±0.04 mV, p=0.32 for FV). Input/output (I/O) curves, which were obtained by plotting the amplitude of FV versus the fEPSP slope, were similar in cDKO and control mice (p=0.32), indicating normal basal synaptic transmission. Paired-pulse facilitation (PPF), a presynaptic form of short-term plasticity, was significantly reduced in PS cDKO mice relative to the control ($F_{(7,476)}$=5.67, p<0.0001), suggesting an increase in probability of neurotransmitter release.

We next explored the effects of presenilin inactivation on synaptic plasticity at CA1 synapses. Long-term potentiation (LTP) is the best-understood model of the experience dependent synaptic strengthening involved in learning and memory (Bailey, et al., *Nat. Rev. Neurosci* 1:11-20. (2000); Malenka, et al., *Science* 285:1870-1874 (1999)). We induced LTP with theta burst stimulation (TBS) and found that induction and maintenance of LTP induced by 5 TBS were reduced in cDKO mice. The magnitude of LTP measured 60 min after TBS in cDKO mice (121.6±4.5%) was significantly lower relative to the control (150.9±8.8%, p<0.002). These results show that loss of presenilin function results in impaired synaptic plasticity, which may underlie the memory impairment exhibited by these mice.

Age-Dependent Neuronal Degeneration in PS cDKO Mice

We next analyzed PS cDKO mice at 6 months of age to investigate the possible age dependent effects of PS inactivation. Nissl staining showed grossly similar brain morphology in cDKO and control mice, but the cerebral cortex of cDKO mice appeared thinner. Quantification of neuronal number in the neocortex of cDKO and control mice revealed an 18% reduction (p<0.01) in cDKO mice. Immunohistochemical analysis showed markedly reduced MAP2 immunoreactivity in the neocortex, indicating dendritic degeneration. The reduction of MAP2 immunoreactivity in hippocampal area CA1 was less clear, though the dendritic morphology appeared disrupted. Synaptophysin immunoreactivity was markedly reduced in hippocampal area CA1, suggesting loss of presynaptic terminals. In addition to synaptic and neuronal loss, cDKO brains at this age exhibit astrogliosis, as indicated by an increase in GFAP immunoreactivity. These results show that PS cDKO mice develop synaptic, dendritic and neuronal degeneration and gliosis between the ages of 2 and 6 months. Previous studies have shown that inactivation of PS1 in cultured cells and adult brain materials results in reduced production of Aβ peptides. Further, inactivation of both presenilins in embryonic stem cells causes complete elimination of secreted extracellular Aβ peptides (Herreman, et al., *Nat. Cell Biol.* 2:461 (2000); Zhang, et al., *Nat. Cell Biol.* 2:463 (2000)). We then measured levels of endogenous mouse Aβ peptides (intracellular and extracellular) in the cortex of cDKO and control mice at 5-6 months of age by enzyme-linked immunosorbent assay (ELISA). Approximately 50% reduction of both Aβ 40 and Aβ 42 peptides were found in the cerebral cortex of cDKO mice relative to the control. The remaining Aβ peptides found in the cortex of cDKO mice could be due to Aβ peptides generated in glial cells or residual Aβ peptides in pyramidal neurons lacking both presenilins, which is consistent with a recent report showing normal generation of intracellular Aβ 42 peptides in the absence of presenilins Wilson, R., *Nat. Neurosci.* 5:849-855 (2002); (Yu, et al., *Neuron* 31, 713-726 (2001)).

Severe Memory Impairment in PS cDKO Mice at 6 Months

To determine whether the ongoing neuronal degeneration in cDKO mice results in severer memory deficits, we tested these mice at 6 months in the water maze task. PS cDKO (n=12), PS1 cKO (n=10) and control (n=10) mice were trained with the same intensive protocol. cDKO mice performed very poorly with significantly longer latencies and path lengths compared to the control and PS1 cKO mice (p<0.0001), whereas PS1 cKO mice performed as well as control mice with similar latencies (p=0.29) and path lengths (p=0.84). The post-training probe trial revealed that control and PS1 cKO mice displayed significantly higher target quadrant occupancies relative to other quadrants (T versus AL, AR or OP; p<0.0001), whereas cDKO mice failed to show such a preference (T versus AL, AR or OP; p>0.05). The number of platform crossings by cDKO mice (0.9±0.3) was much lower than that of control (4.8±0.6) and PS1 cKO (4.1±0.8) mice (p<0.0001). All three groups performed well in the visible platform test with similarly low latencies. These results demonstrate substantial deterioration in the spatial memory performance of cDKO mice between 2 and 6 months of age.

We further examined cDKO (n=11), PS1 cKO (n=9) and control (n=10) mice at 6 months in contextual fear conditioning. Although all three groups displayed similar levels of freezing immediately after training (p=0.44), cDKO mice (12.1±5.4%) showed significantly reduced levels of freezing to the context 24 hours following training compared to control (50.1±8.5%) and PS1 cKO (52.9±5.2%) mice (p<0.001).

Consistent with neurodegeneration revealed by the morphological analysis, the water maze and fear conditioning results together demonstrate that cDKO mice exhibit more severe memory impairments at 6 months of age than they did at 2 months of age.

Severe Synaptic Dysfunction in PS cDKO Mice at 6 Months

We further examined these mice at 6 months of age for deficits in synaptic transmission and plasticity in the Schaeffer collateral pathway. In cDKO mice the maximal fEPSP was normal (2.0±0.3 V/sec) compared to control mice (2.3±0.2, p=0.36), but the maximal FV was significantly reduced (p<0.02), indicating that fewer axons were recruited upon stimulation. Input/output curves were elevated in cDKO mice (p<0.001), indicating enhanced basal synaptic transmission. Paired-pulse facilitation was significantly reduced in cDKO mice relative to the control ($F_{(6, 270)}$=5.89, p<0.0001). Further, LTP induced by 5 TBS was dramatically reduced in cDKO mice. The magnitude of LTP measured 60 min after TBS in cDKO mice (127.0±6.6%) was significantly lower relative to the control (174.2±8.7%, p<0.0004).

We further investigated whether PS cDKO mice display alterations in long-term depression (LTD), which is involved in the bidirectional modulation of synaptic efficacy (Bear, *Proc. Natl. Acad. Sci. USA* 96:9457-9458 (1999)). We induced LTD with paired-pulse low-frequency stimulation (ppLFS), which has been shown to induce LTD effectively in slices of mature mice (Thiels, et al., *J. Neurophysiol.* 72:3009-3016 (1994); Kemp, et al., *Neuropharmacology* 36:397-399 (1997)). The induction and maintenance of LTD were unaffected in cDKO mice. The magnitude of LTD measured 75 min after conditioning in cDKO mice (81.9±4.2%) was similar to that in the control (79.6±4.2%, p=0.71). Thus, loss of presenilin function affects LTP but not LTD, indicating a selective rather than general impairment in synaptic plasticity. It is plausible that changes in calcium homeostasis due to loss of presenilins (Yoo, et al., *Neuron* 27:561-572 (2000)) affect LTP induction preferentially, which requires a higher calcium threshold than LTD (Bear, *Proc. Natl. Acad. Sci. USA* 96:9457-9458 (1999)).

Cerebral Atrophy in PS cDKO Mice at 9 months

To determine if neurodegeneration progressed in an age-dependent manner, we extended our morphological analysis of cDKO mice to 9 months of age. Nissl staining revealed cerebral atrophy, including thinner cortical layers and enlarged ventricles. Stereological quantification of cDKO (n=4) and control (n=4) brains showed a 24% reduction in neuronal number (p<0.04) and a 35% decrease in cortical volume (p<0.0007) in the neocortex of cDKO mice. The reduction in MAP2 immunoreactivity was more dramatic in the neocortex than in hippocampal area CA1. To determine whether the slight reduction in MAP2 immunoreactivity in hippocampal area CA1 indeed reflected a quantitative decrease in dendritic processes, we performed Golgi staining and confirmed a reduction in the dendritic complexity and spine density of CA1 pyramidal neurons. Quantification CA1 pyramidal neurons (n=40 for cDKO; n=30 for control) of cDKO (n=4) and control (n=3) brains further revealed a 25% reduction in the total length of both apical and basal dendrites (p<0.0005), 15% and 11% decreases in branch points of apical (p<0.001) and basal dendrites (p<0.02), respectively. Gliosis at this age became even more dramatic than that at 6 months, demonstrating an age-dependent inflammatory response in cDKO brains. Collectively, these results document age-dependent, progressive neurodegeneration and dementia in mice lacking presenilins in excitatory neurons of the forebrain. Western analysis of cDKO brain lysate also showed increased levels of the C-terminal fragment of N-Cadherin, Nectin 3 and LRP, suggesting that accumulation of these products may be used as biomarkers for neurodegeneration.

C. Discussion

At two months of age, in the absence of neuropathological changes, PS cDKO mice exhibited impairments in spatial and associative memory, accompanied by deficits in synaptic plasticity. Between the ages of 2 and 6 months, PS cDKO mice develop synaptic, dendritic and neuronal degeneration and a marked deterioration in spatial memory performance. In addition to impairments in synaptic plasticity, basal synaptic transmission is altered at 6 months of age. The enhanced synaptic transmission could represent a compensatory effect due to loss of presynaptic axonal terminals, as indicated by reduced synaptophysin immunoreactivity in hippocampal CA1 presynaptic terminals and reduced fiber volley amplitude.

By the age of 9 months, cDKO mice develop striking cerebral atrophy, gliosis, dramatic loss of dendrites and spines, marked thinning of the neocortex and enlargement of the ventricles, with the reductions in neuronal number and cortical volume reaching 24% and 35%, respectively. These results demonstrate essential roles of presenilins in synaptic function and maintenance of neuronal integrity and survival in the adult brain. The striking age-dependent neuronal degeneration observed in cDKO mice resembles the characteristic neuropathology of AD in several respects. First, the neurodegeneration occurs slowly and progressively during adulthood, with an onset between 2 and 6 months of age and gradual worsening thereafter. Second, the neuronal loss affects substantial proportions of cerebral cortical neurons in a diffuse manner, and is accompanied by considerable cerebral atrophy. The decrements in neuron number and brain volume are comparable to those observed in AD cases (Brun, et al., *Histopath* 5:549-564 (1981)). Third, consistent with neuropathological studies of AD, neurodegeneration is also manifested by a number of morphological abnormalities that presumably precede frank neuronal death, including dendritic atrophy and synaptic loss (Hanks, *Brain Res.* 540:63-82 (1991) Braak, et al., *Acta Neuropathol. (Berl)* 93:323-325 (1997); Terry, et al., *Ann. Neurol.* 30:572-580 (1991)). Fourth, the neurodegenerative process incites a marked diffuse inflammatory response in the form of reactive astrogliosis.

Lastly, the age-related deterioration of memory impairment and synaptic dysfunction, likely resulting from the ongoing synaptic and neuronal degeneration, parallels the progressive cognitive decline in AD patients. The amyloid deposition characteristic of AD neuropathology, however, is absent in PS cDKO mice. In fact, levels of Aβ peptides are markedly reduced in the cerebral cortex. Nevertheless, loss of presenilin function in cDKO mice is sufficient to recapitulate many of the central features of Alzheimer's disease, most notably profound neuronal degeneration. The central importance of neurodegeneration in AD is emphasized by neuropathological studies demonstrating that synaptic and neuronal loss correlate well with the severity of dementia, while indices of amyloid accumulation do not (Gomez-Isla, et al., *Ann. Neurol.* 41:17-24 (1997); Hyman, et al., *Curr. Opin. Neurol. Neurosurg.* 5:88-93 (1992)). Such profound neuronal degeneration has not been reproduced in transgenic mice overexpressing FAD-linked mutant amyloid precursor protein (APP), despite accumulation of very high levels Aβ peptides and heavy loads of amyloid plaques (Games, et al., *Nature* 373:523-527 (1995); Masliah, et al., *J. Neurosci.* 16:5795-5811 (1996); Hsiao, et al., *Science* 274:99-102 (1996); Irizarry, et al., *J. Neuropath. Exp. Neurol.* 56:173-177 (1997)). These APP transgenic mice display several features of AD, such as memory impairment, synaptic dysfunction, amyloid deposition, neuritic degeneration and plaque-associated gliosis. The development of profound synaptic, dendritic and neuronal loss in PS cDKO mice despite a marked reduction in amyloid peptides suggests that AD-like neurodegeneration may occur through an amyloid-independent mechanism. The fact that both models result in approximation of AD in mice strongly suggests that both contribute to the disease in humans.

All references cited herein are fully incorporated by reference. Having now fully described the invention, it will be understood by one of ordinary skill in the art that the invention may be performed within a wide and equivalent range of conditions, parameters and the like, without affecting the spirit or scope of the invention or any embodiment thereof.

What is claimed is:

1. A presenilin-deficient mouse made by a method comprising:
   (a) making a first recombinantly engineered mouse whose genomic DNA comprises:
      (i) homozygous modified endogenous presenilin-1 alleles in which one or more exons of each presenilin-1 allele are flanked by lox P elements in such a manner that, upon exposure to Cre recombinase, said one or more exons are excised from said genomic DNA;
      (ii) a DNA sequence element coding for Cre recombinase under the control of a CaM kinase II promoter;
   (b) producing or obtaining a second recombinantly engineered mouse, whose genomic DNA comprises homozygous modified endogenous presenilin-2 alleles in which one or more exons have been interrupted by the introduction of an exogenous sequence that prevents each presenilin-2 allele from expressing a functional protein;
   (c) crossbreeding said first recombinantly engineered mouse with said second recombinantly engineered mouse to produce a progeny mouse whose genomic DNA comprises a presenilin-1 allele with exons flanked by loxP elements as described above in paragraph (a)(i); a DNA sequence element coding for Cre recombinase as described in paragraph (a)(ii); and a presenilin-2 allele in which one or more exons have been interrupted as described in paragraph (b);
   (d) further breeding said progeny mouse to produce a presenilin-deficient mouse whose genomic DNA comprises homozygous presenilin-1 alleles with exons flanked by loxP elements as described in paragraph (a)(i); a DNA sequence element coding for Cre recombinase as described in paragraph (a)(ii); and homozygous presenilin-2 alleles in which one or more exons have been interrupted as described in paragraph (b);
   and wherein, at some time after birth and prior to death, said presenilin-deficient mouse comprises within the genome of cells having CaM kinase II promoter activity a homozygous deletion within its presenilin-1 alleles such that, compared to a wild type mouse, said presenilin-deficient mouse is:
(i) deficient in presenilin-1 in those cells where the CaM kinase II promoter is active;
(ii) does not express presenilin-2; and
(iii) exhibits age-dependent synaptic and neuronal degeneration and age-related memory impairment.

2. The presenilin-deficient mouse of claim 1, wherein said loxP elements are located in introns 1 and 3 of said presenilin-1 alleles.

3. The presenilin-deficient mouse of claim 2, wherein:
(a) there is one loxP element in said intron 1;
(b) said intron 3 further comprises a marker DNA sequence coding for a hygromycin resistance protein and coding for thymidine kinase, both of which are under the control of a CMV promoter;
(c) there are two loxP elements in intron 3, one lying 5' to said marker DNA sequence and one lying 3' to said marker DNA sequence.

4. The presenilin-deficient mouse of claim 3, wherein said exogenous sequence that prevents said presenilin-2 alleles from producing a functional protein is in exon 5 of said presenilin-2 alleles.

5. The presenilin-deficient mouse of claim 3, wherein said exogenous sequence comprises a neomycin resistance gene under the control of an exogenous promoter.

6. The presenilin-deficient mouse of claim 1 wherein:
a) said presenilin-deficient mouse is viable for at least six months after birth, and
b) said presenilin-deficient mouse makes normal levels of presenilin-1 up until at least the time of its birth.

7. A transgenic mouse useful in the making of the presenilin-deficient mouse of claim 1, comprising within its genomic DNA:
(a) a presenilin-1 gene in which one or more exons of said gene are flanked by loxP elements in such a manner that, upon exposure to Cre recombinase, said one or more exons are excised from said genomic DNA; and
(b) a DNA sequence element coding for Cre recombinase under the control of a CaM kinase II promoter.

8. The transgenic mouse of claim 7, wherein said loxP elements are in intron 1 and intron 3 of said presenilin-1 gene.

9. The transgenic mouse of claim 7, wherein:
(a) there is one loxP element in intron 1; and
(b) there is at least one loxP element in intron 3.

* * * * *